United States Patent [19]

Poncept

[11] Patent Number: 4,592,227

[45] Date of Patent: Jun. 3, 1986

[54] APPARATUS FOR ANALYSIS OF BLOOD

[76] Inventor: Gérard Poncept, 10, Chemin de Dalibray, Gaillonnet par Seraincourt 95450 - Vigny, France

[21] Appl. No.: 560,477

[22] Filed: Dec. 12, 1983

[30] Foreign Application Priority Data

Dec. 17, 1982 [FR] France .............................. 82 21221

[51] Int. Cl.$^4$ ...................... G01N 15/05; G01N 33/49
[52] U.S. Cl. ..................................... 73/61.4; 141/59; 141/113; 215/311; 422/68; 422/73; 436/70
[58] Field of Search .......................... 73/61.4; 436/70; 422/68, 73, 99, 102, 103; 215/307, 311; 53/264, 268, 319, 489; 141/1, 59, 113, 237, 275, 284

[56] References Cited

U.S. PATENT DOCUMENTS

| | | |
|---|---|---|
| 2,729,971 | 1/1956 | Stein ..................................... 73/61.4 |
| 3,026,717 | 3/1962 | Danielsson et al. ................. 73/61.4 |
| 3,373,601 | 3/1968 | Monn ................................... 73/61.4 |
| 3,734,079 | 5/1973 | Weber ............................... 422/73 X |
| 3,827,286 | 8/1974 | Bond et al. ........................... 73/61.4 |
| 3,955,423 | 5/1976 | Ohringer ......................... 436/180 X |
| 4,197,735 | 4/1980 | Munzer et al. ....................... 73/61.4 |
| 4,353,246 | 10/1982 | Farber et al. ....................... 73/61.4 |

FOREIGN PATENT DOCUMENTS 0978379 4/1951 France ................................. 73/61.4
0726095 3/1955 United Kingdom ................. 73/61.4

Primary Examiner—Barry S. Richman
Assistant Examiner—Robert J. Hill, Jr.
Attorney, Agent, or Firm—Brisebois & Kruger

[57] ABSTRACT

Apparatus for determining sedimentation rates including a first support means having a plurality of tubes, held vertically and spaced, and a second support means having a plurality of tubes, of larger diameter than the tubes mounted on the first support means, and each able to receive a blood sample, the tubes being vertical and spaced on the said second support means, and a single suction device mounted at the upper end of the first support means, the support means being movable with respect to each other between a first position in which the tubes of the first support means are separated from the tubes of the second support means, a second position in which the lower ends of the tubes of the first support means dip into the tubes of the second support means, and a third position in which the sedimentation of the red blood corpuscles takes place. The apparatus includes tubular elastic sleeves mounted on the lower ends of the tubes on the first support and means are provided in the tubes on the second support for deforming the tubular elastic sleeves to seal the lower ends of the tubes on the first support when said support means are in the third position.

4 Claims, 8 Drawing Figures

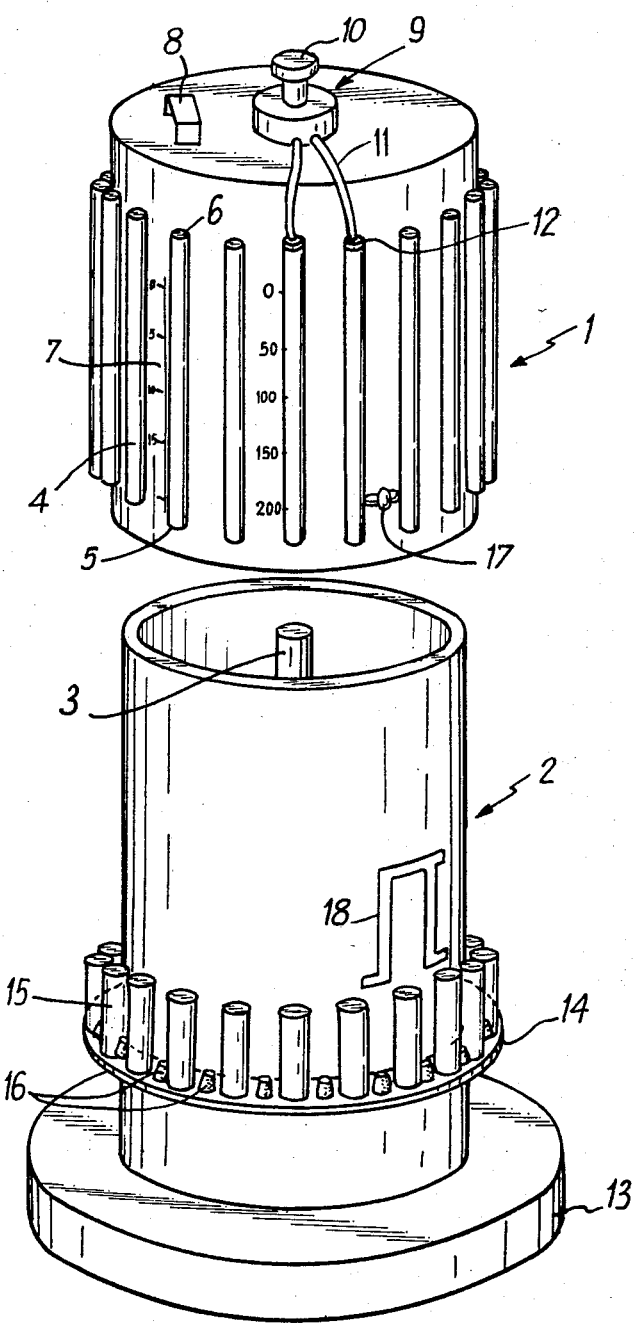

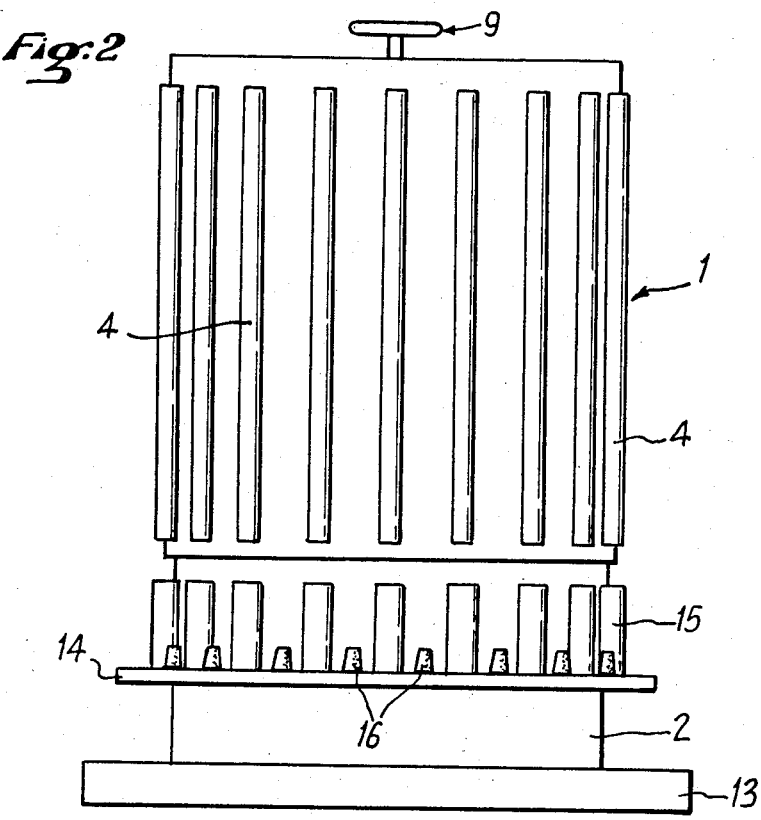
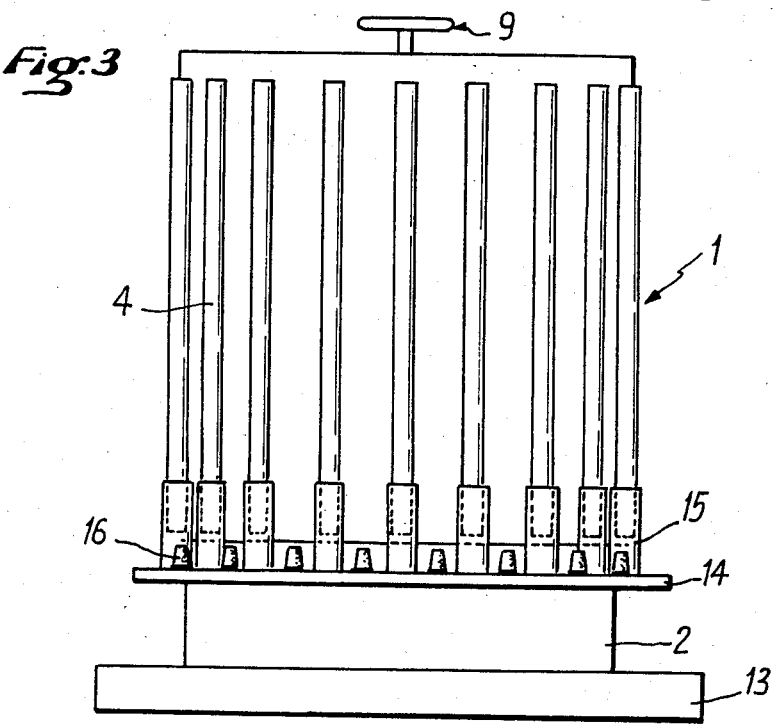

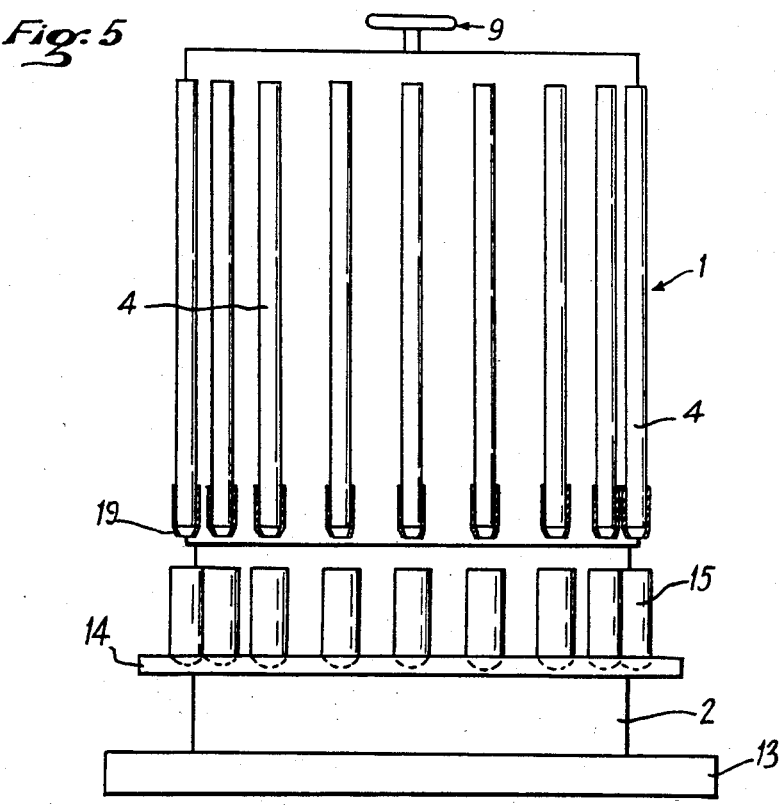
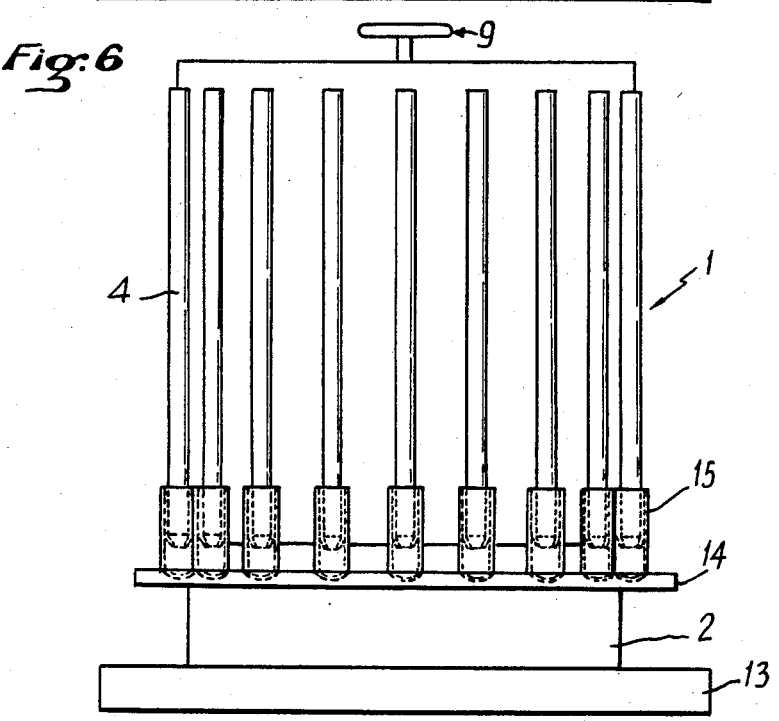

APPARATUS FOR ANALYSIS OF BLOOD

The present invention relates to medical analyses apparatus and more specifically to blood analysis apparatus to permit determination of sedimentation rates, as well as a method of using the apparatus.

Traditionally, the sedimentation rate is measured by use of a Westergreen tube or pipette, that is, a thin graduated tube open at both ends. The technician first dips such a tube in a tube of larger diameter containing a blood sample, then sucks up the blood from the upper end of the Westergreen tube to a specified upper reference gradation of this tube. The lower end of the tube is then closed and the tube is placed on a support. Timed readings are then taken, the first usually at the end of one hour and the second at the end of two hours, of the level of red blood corpuscle sedimentation in the tube. After the analysis, the tubes which were used are rinsed.

It is clear that for a medical analysis laboratory handling a large number of rate sedimentation tests daily, the process just described must be repeated as many times as there are blood samples to be analyzed. In addition to the fact that this process is relatively time consuming, it also involves a medical danger for the technician who must orally suck up the blood from the tubes containing the blood samples, to the appropriate level in the Westergreen tubes, and who may in case of poorly judged suction ingest contaminated blood.

U.S. Pat. No. 3,827,286 has already shown an apparatus for determination of sedimentation rates which includes a first support means having several graduated tubes, open at both ends and held vertically at intervals on the support means, and a second support means having several tubes of larger diameter than the tubes mounted on the first support means and each able to receive a blood sample, the tubes being vertical and spaced along the said second support means, and a single suction device mounted at the upper end of the first support means and able to be connected to the upper end of each of the tubes of the first support means. The support means are movable with respect to each other between a first position in which the tubes of the first support means are separated from the tubes of the second support means, and a second position in which the lower end of the tubes of the first support means are immersed in the tubes of the second support means.

The graduated tubes are then again moved vertically upward and the sedimentation of the red blood corpuscles is allowed to proceed in these tubes, followed by the usual level readings at predetermined intervals.

The essential disadvantage of the apparatus described in the prior document is that suction is maintained in the graduated tubes during the sedimentation phase which, on the one hand, in view of the relatively long reading periods, make the action of the suction device very important, but which above all risks accidental escape of the blood due to failure of the suction device.

The disadvantage of an accidental escape is obvious for the personnel required to carry out the analyses and all the more when the blood to be analyzed presents the danger of contamination.

The present invention proposes to provide an apparatus eliminating the above mentioned disadvantages and risks.

The apparatus according to the invention is essentially characterized by the fact that it comprises a plurality of stopper elements, able to hermetically seal the lower openings of the tubes mounted on the first support means, the support means being movable with respect to each other to a third position in which the tubes of the first support means coact with the stopper elements to obtain an hermetic seal of their lower end by the stopper elements.

According to the present invention, the suction device is thus operated only when the support means are in the second position to fill each of the tubes of the first support means to a predetermined upper reference level, suction being maintained until the support means are brought into the third position. Suction is then, on the other hand, discontinued during the red blood corpuscle sedimentation phase during which the support means are kept in their third position until reading of the red blood corpuscle sedimentation level is completed.

In a first embodiment, the stopper elements take the form of corks mounted on the second support means, and have dimensions corresponding to the lower openings of the tubes mounted on the first support means to provide tight sealing of the lower ends of the tubes when they are lowered onto the corks.

In a second embodiment, the stopper elements are each formed from an elastic tubular sleeve tightly gripping the lower end of each of the tubes of the first of the first support means, extending from the lower end of the tubes, and coacting with a wall of the tubes of the second support means to seal the lower end of the tubes of the first support means when these latter are brought to the vicinity of the bottom of the tubes of the second support means, which is the position in which the sedimentation of the red blood corpuscles takes place in this second embodiment.

In one particularly useful embodiment of the apparatus, the support means are made in the form of cylinders of circular section at the periphery of which are mounted respectively the tubes and if necessary the stopper elements.

Preferably according to the invention, the suction device is mounted at the upper end of the first support means, this suction device being of any appropriate type, for example, a piston sliding in a cylinder, a three-valve suction bulb, a vacuum pump provided if necessary with a filter, and driven by a micromotor.

The apparatus according to the invention is advantageously completed for cleaning, by a tank in which the entire apparatus can be immersed after the analyses have been finished, the suction device then being advantageously used to clean the tubes while the device is immersed in the water contained in the tank.

Other advantages and characteristics of the invention will become apparent from the following description of a totally non-limiting embodiment with reference to the attached drawings in which:

FIG. 1 shows schematically in exploded perspective, one embodiment of the apparatus according to the invention;

FIGS. 2 to 4 show schematically, the apparatus of FIG. 1, in three operating positions;

FIGS. 5 to 7 show an apparatus according to a second embodiment, in the three operating positions.

Figure 4:
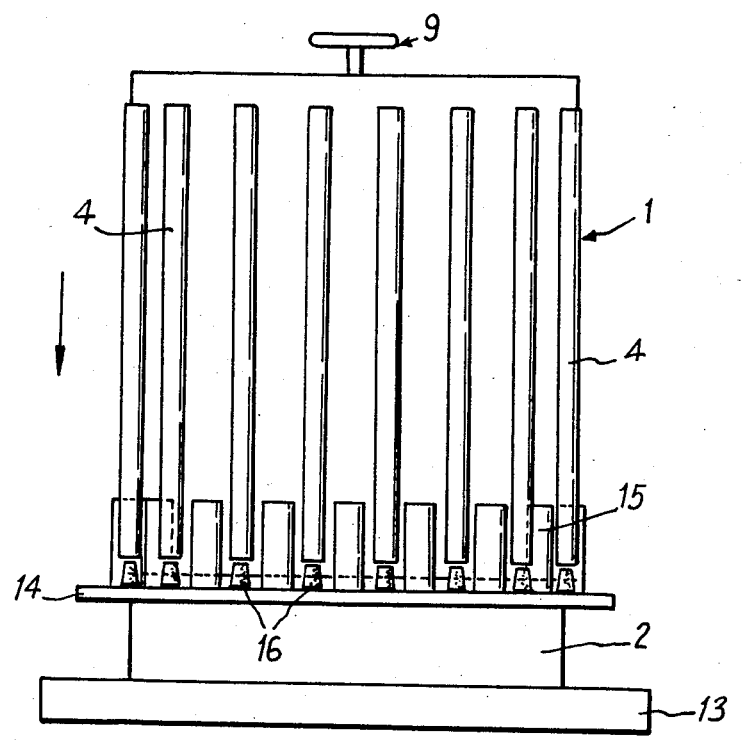
Figure 7:
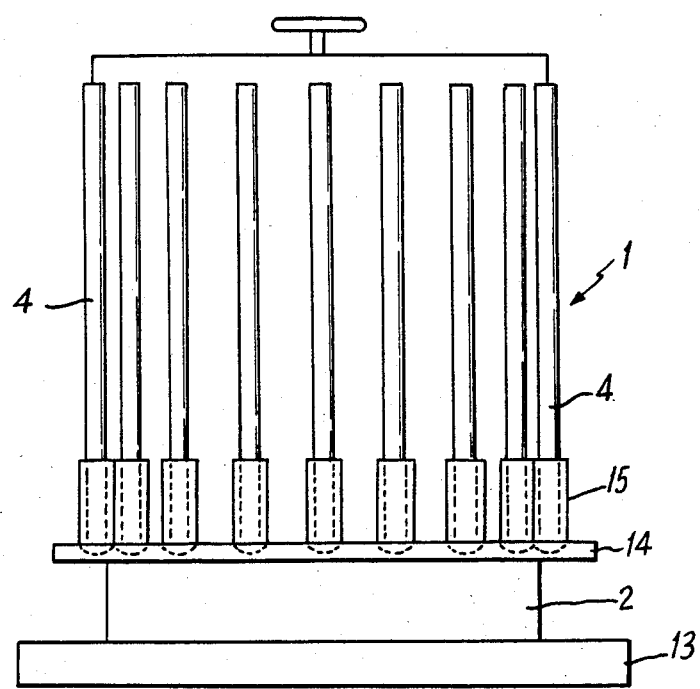

The apparatus according to the invention shown at FIG. 1 basically includes two cylinders of circular section 1 and 2, the upper cylinder 1 being able to be fitted on lower cylinder 2, the two cylinders being thus mounted concentrically around an axle 3.

Upper cylinder 1 serves as a support for a number of Westergreen tubes 4, for example twenty-five, the tubes 4 being spaced around the periphery of cylinder 1.

Each of the tubes 4 is open at its lower end 5, and upper end 6. Each tube is graduated and, preferably, there is also a corresponding graduation 7 on the wall of the cylinder.

On the upper surface of cylinder 1 there is a grasping means such as handle 8 and a suction device designated overall by 9 and which, in the example shown, is comprised of a piston slidable in a cylinder and operated by means of a knurled screw 10. The suction device 9 is connected to each of the upper ends 6 of Westergreen tubes 4, by flexible tubing 11 supplied with a cap 12 sealing the upper end 6 of each tube.

Lower cylinder 2 has a base 13 and an annular flange 14 on which are alternately mounted, test tubes or containers 15 each able to receive a blood sample, and stoppers 16 each able to tightly seal lower end 5 of Westergreen tubes 4. The number of tubes 15 and stoppers 16 equals the number of Westergreen tubes 4 of first cylinder 1, which is twenty-five in the example shown.

It is advantageous to provide, according to the invention, to hold upper cylinder 1 in is predetermined positions relative to lower cylinder 2, an arrangement comprised of a rod extending diametrically of cylinder 1, projecting to its exterior wall, as shown at 17 on FIG. 1, the rod being able to slide in diametrically opposed slots 18 made in the wall of lower cylinder 2, each slot having several vertical and horizontal sections.

One method of using the apparatus according to the invention will now be described with reference to FIGS. 2 to 4.

As is shown on FIG. 2, cylinder 1 is first placed in its top position with respect to cylinder 2 so as to allow placement of tubes 15 containing the blood samples at their respective positions on flange 14 of cylinder 2.

Cylinder 1 is then lowered with respect to cylinder 2 so as to bring it into the position shown on FIG. 3 in which each of the Westergreen tubes 4 of cylinder 1 dips into a tube 15 of cylinder 2.

By means of suction device 9, a predetermined amount of blood is drawn up in each of the Westergreen tubes 4 to the upper reference level corresponding to the value 0 (FIG. 1), after which, while suction is maintained, cylinder 1 is turned with respect to cylinder 2 so as to bring Westergreen tubes 4 just above stoppers 16, as is shown on FIG. 4, following which cylinder 1 is lowered to engage each of the tubes 4 on a cork 16.

Suction is then stopped. The device is thus in measurement position and the level of sedimentation of the red blood corpuscles in tubes 4 can then be noted at appropriate time intervals either by reading the gradations of each tube or by reference to the gradations on measuring scale 7 on the upper cylinder.

Once the analysis is finished, tubes 15 are removed and the entire apparatus is placed in a tank with circulating water in which tubes 4 and the rest of the apparatus can be rinsed by advantageously using for this purpose suction device 9 to create a circulation of water in the tubes.

The apparatus shown on FIGS. 5 to 8 has an overall structure similar to that described on the preceding figures, but is basically distinguished by the nature of the stopper elements and the movements allowing sealing of tubes 4 by the stopper elements.

In this embodiment, instead of having several stoppers 16 mounted on flange 14, the apparatus has several elastic tubular sleeves 19 mounted to tightly grip the lower ends of tubes 4, and to extend from the said lower ends, and preferably comprising an end of reduced section.

To use the apparatus of the embodiment of FIGS. 5 to 8, at first the procedure is the same as for the first embodiment with respect to placing the tubes 15 containing the blood samples in their respective positions on flange 14 of cylinder 2.

Cylinder 1 is then lowered with respect to cylinder 2 to bring it into the position shown on FIG. 6 in which each of the Westergreen tubes 4 of cylinder 1 dips into a tube 15 of cylinder 2.

Figure 8:
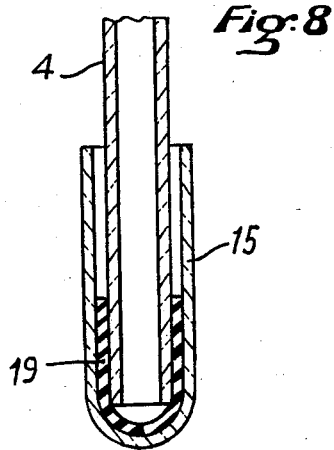
FIG. 8 shows, in enlarged section, the disposition of the tubes in the third position.

By means of suction device 9, a predetermined amount of blood is then drawn up in each of the Westergreen tubes 4 to the upper reference level corresponding to the value 0, after which, while maintaining suction, cylinder 1 is lowered with respect to cylinder 2 so as to bring Westergreen tubes 4 near the bottom of tubes 15 which, as will be best seen on FIG. 8, causes sleeves 19 to take the shape of the lower wall of tubes 15 and ensures sealing of the lower end of tubes 4.

Then suction is then stopped and sedimentation of red blood corpuscles is allowed to proceed.

Although the invention has been described in connection with particular embodiments, it is evident that it is in no way thereby limited and may undergo numerous variations and modifications without departing from either its scope or its spirit.

I claim:

1. Apparatus for determining corpuscle sedimentation rates comprising, first support means supporting a plurality of graduated tubes having upper and lower ends, said tubes being held vertically and spaced apart horizontally on said first support means, second support means supporting a plurality of containers having open upper ends and closed lower ends and being of a size such that the lower ends of said tubes can be inserted into the containers for receiving blood samples, said containers being held generally vertically and spaced apart horizontally on said second support means such that said containers are in respective alignment with said tubes, said first and second support means being movable with respect to each other to a first position in which the tubes on the first support means are spaced from the containers on the second support means, a second position in which the lower ends of the tubes on the first support means extend into the containers on the second support means, and a third position in which sedimentation of blood within said graduated tubes can occur, suction means for applying a suction to the upper ends of said tubes to draw blood samples into the tubes from said containers when said support means are in said second position, and seal means for sealing the lower ends of the tubes to prevent loss of blood samples from said tubes when said support means are in said third position, said seal means comprising a tubular elastic sleeve mounted on the lower end of each of the tubes, and extending downwardly from the lower ends of the tubes, wherein said first support means is moved downwardly from said second position to said third position, and means in said containers for deforming the tubular elastic sleeves to seal the lower ends of the tubes in said third position of the support means, said suction means maintaining suction in said tubes at least until said support means are moved to said third position.

2. Apparatus according to claim 1 wherein said first support means comprises a circular cylinder, said second support means comprises a circular support concentric with said cylinder, said tubes are mounted around said cylinder, and said containers are on said circular support in axially aligned relation, respectively, to said tubes.

3. Apparatus according to claim 1 wherein said suction means comprises suction means mounted on an upper end of said first support means.

4. Apparatus according to claim 3 wherein said means in said containers comprises the closed lower ends of the containers.

* * * * *